United States Patent [19]
Freyne et al.

[11] Patent Number: 6,051,718
[45] Date of Patent: Apr. 18, 2000

[54] PDE IV INHIBITING 2-CYANOIMINOIMIDAZOLE DERIVATIVES

[75] Inventors: Eddy Jean Edgard Freyne, Rumst, Belgium; Francisco Javier Fernández-Gadea, Toledo; José Ignacio Andrés-Gil, Madrid, both of Spain

[73] Assignee: Janssen Pharmaceutica, N.V., Beerse, Belgium

[21] Appl. No.: 09/147,925

[22] PCT Filed: Sep. 24, 1997

[86] PCT No.: PCT/EP97/05322

§ 371 Date: Mar. 19, 1999

§ 102(e) Date: Mar. 19, 1999

[87] PCT Pub. No.: WO98/14432

PCT Pub. Date: Apr. 9, 1998

[30] Foreign Application Priority Data

Oct. 2, 1996 [EP] European Pat. Off. .............. 96202749

[51] Int. Cl.$^7$ ...................... C07D 233/32; C07D 233/36; C07D 233/38; C07D 233/70; C07D 221/02; A61R 31/4168; A61R 31/438

[52] U.S. Cl. ................... 548/316.1; 514/299; 514/393; 514/398; 546/112; 548/331.5

[58] Field of Search ............................. 548/331.5, 316.1; 514/398, 393, 299; 546/112

[56] References Cited

U.S. PATENT DOCUMENTS 4,880,933  11/1989  Shiokawa et al. ................... 544/332

FOREIGN PATENT DOCUMENTS

| WO 93/04032 | 3/1993 | WIPO ................. 548/331.5 |
| WO 94 02465 | 2/1994 | WIPO . |
| WO 94 12461 | 6/1994 | WIPO . |
| WO 94 20455 | 9/1994 | WIPO . |
| WO 95 04045 | 2/1995 | WIPO . |
| WO 95 05386 | 2/1995 | WIPO . |
| WO 95 20578 | 8/1995 | WIPO . |
| WO 96 00218 | 1/1996 | WIPO . |
| WO 96 31485 | 10/1996 | WIPO . |
| WO 96 31486 | 10/1996 | WIPO . |
| WO 96 31487 | 10/1996 | WIPO . |

*Primary Examiner*—Floyd D. Higel
*Attorney, Agent, or Firm*—Mary A. Appollina

[57] ABSTRACT

The present invention concerns 2-cyanoiminoimidazole derivatives having the formula

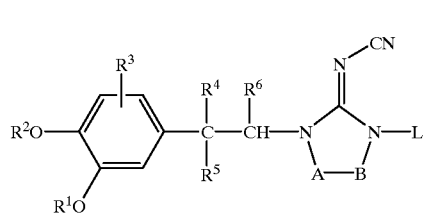

(I)

the N-oxide forms, the pharmaceutically acceptable addition salts and the stereochemically isomeric forms thereof, wherein $R^1$ and $R^2$ each independently are hydrogen; $C_{1-6}$alkyl; difluoromethyl; trifluoromethyl; $C_{3-6}$cycloalkyl; a saturated 5-, 6- or 7-membered heterocycle containing one or two heteroatoms selected from oxygen, sulfur or nitrogen; indanyl; 6,7-dihydro-5H-cyclopentapyridinyl; bicyclo[2.2.1]-2-heptenyl; bicyclo[2.2.1]heptanyl; $C_{1-6}$alkylsulfonyl; arylsulfonyl; or substituted $C_{1-10}$alkyl; $R^3$ is hydrogen, halo or $C_{1-6}$alkyloxy; $R^4$ is hydrogen; halo; $C_{1-6}$alkyl; trifluoromethyl; $C_{3-6}$cycloalkyl; carboxyl; $C_{1-4}$alkyloxycarbonyl; $C_{3-6}$cycloalkylaminocarbonyl; aryl; $Het^1$; or substituted $C_{1-6}$alkyl; or $R^4$ is —O—$R^7$ or —NH—$R^8$; $R^5$ is hydrogen, halo, hydroxy, $C_{1-6}$alkyl or $C_{1-6}$alkyloxy; $R^6$ is a hydrogen or $C_{1-4}$alkyl; or $R^4$ and $R^6$, or $R^4$ and $R^5$ taken together may form a bivalent radical; —A—B— is —$CR^{10}$=$CR^{11}$— or —$CHR^{10}$—$CHR^{11}$—; L is hydrogen; $C_{1-6}$alkyl; $C_{1-6}$alkylcarbonyl; $C_{1-6}$alkyloxycarbonyl; substituted $C_{1-6}$alkyl; $C_{3-6}$alkenyl; substituted $C_{3-6}$alkenyl; piperidinyl; substituted piperidinyl; $C_{1-6}$alkylsulfonyl or arylsulfonyl; having PDE IV and cytokine inhibiting activity. The invention also relates to processes for preparing the compounds of formula (I) and pharmaceutical compositions thereof.

9 Claims, No Drawings

PDE IV INHIBITING 2-CYANOIMINOIMIDAZOLE DERIVATIVES

CROSS REFERENCE TO RELATED APPLICATIONS

This application is a National Stage application under 35 U.S.C. 371 of PCT/EP97/05322 filed Sep. 24, 1997, which claims priority from EP 96.202.749.6, filed Oct. 2, 1996.

The present invention concerns 2-cyanoiminoimidazole derivatives having phosphodiesterase IV (PDE IV) and cytokine inhibiting activity and their preparation; it further relates to compositions comprising them, as well as their use as a medicine.

WO 95/05386, published on Feb. 23, 1995 by Smithkline Beecham Corporation, discloses phenethylamine derivatives, such as N-[2-(3-cyclopentyloxy-3-methoxyphenyl)ethyl]imidodicarbamide and N'-cyano-1-[2-(3-cyclopentyloxy-4-methoxyphenyl)ethyl]carboximidamide, useful for treating phosphodiesterase IV related disease states. It also generically discloses phenethylamine derivatives containing a cyanoguanidine moiety.

The compounds of the present invention differ structurally from art-known PDE IV inhibitors by the fact that they invariably contain a 2-cyanoiminoimidazole moiety. They have therapeutical utility in the treatment of disease states related to an abnormal enzymatic or catalytic activity of PDE IV, and/or disease states related to a physiologically detrimental excess of cytokines, in particular allergic, atopic and inflammatory diseases. The present compounds also have few gastro-intestinal side-effects which are often associated with PDE IV inhibitors.

The present invention concerns 2-cyanoiminoimidazole derivatives having the formula

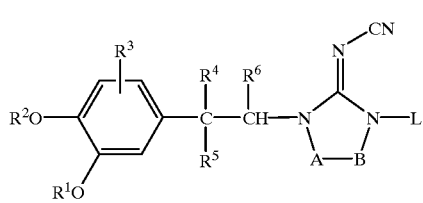

(I)

the N-oxide forms, the pharmaceutically acceptable acid or base addition salts and the stereochemically isomeric forms thereof, wherein: $R^1$ and $R^2$ each independently are hydrogen; $C_{1-6}$alkyl; difluoromethyl; trifluoromethyl; $C_{3-6}$cycloalkyl; a saturated 5-, 6- or 7-membered heterocycle containing one or two heteroatoms selected from oxygen, sulfur or nitrogen; indanyl; 6,7-dihydro-5H-cyclopentapyridinyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, indanyl, 6,7-dihydro-5H-cyclopentapyridinyl, $C_{3-7}$cycloalkyl and a saturated 5-, 6- or 7-membered heterocycle containing one or two heteroatoms selected from oxygen, sulfur or nitrogen;

$R^3$ is hydrogen, halo or $C_{1-6}$alkyloxy;

$R^4$ is hydrogen; halo; $C_{1-6}$alkyl; trifluoromethyl; $C_{3-6}$cycloalkyl; carboxyl; $C_{1-4}$alkyloxycarbonyl; $C_{3-6}$cycloalkylaminocarbonyl; aryl; Het$^1$; or $C_{1-6}$alkyl substituted with cyano, amino, hydroxy, $C_{1-4}$alkylcarbonylamino, aryl or Het$^1$; or $R^4$ is a radical of formula:

—O—R$^7$ (a-1); or

—NH—R$^8$ (a-2);

wherein $R^7$ is hydrogen; $C_{1-6}$alkyl; $C_{1-6}$alkyl substituted with hydroxy, carboxyl, $C_{1-4}$alkyloxycarbonyl, amino, mono- or di($C_{1-4}$alkyl)amino, Het$^1$ or aryl;

$R^8$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{1-4}$alkyl)amino, Het$^1$ or aryl;

$R^5$ is hydrogen, halo, hydroxy, $C_{1-6}$alkyl or $C_{1-6}$alkyloxy; or $R^4$ and $R^5$ taken together may form a bivalent radical of formula:

—(CH$_2$)$_n$— (b-1);

—CH$_2$—CH$_2$—O—CH$_2$—CH$_2$— (b-2);

—CH$_2$—CH$_2$—N(R$^9$)—CH$_2$—CH$_2$— (b-3); or

—CH$_2$—CH=CH—CH$_2$— (b-4);

wherein n is 2, 3, 4 or 5;

$R^9$ is hydrogen, $C_{1-6}$alkyl, $C_{1-6}$alkylsulfonyl or p-toluenesulfonyl;

$R^6$ is a hydrogen or $C_{1-4}$alkyl; or $R^4$ and $R^6$ taken together may form a bivalent radical of formula —(CH$_2$)$_m$—;

wherein m is 1, 2, 3 or 4;

—A—B— is a bivalent radical of formula:

—CR$^{10}$=CR$^{11}$— (c-1); or

—CHR$^{10}$—CHR$^{11}$— (c-2);

wherein each $R^{10}$ and $R^{11}$ independently is hydrogen or $C_{1-4}$alkyl; and L is hydrogen; $C_{1-6}$alkyl; $C_{1-6}$alkylcarbonyl; $C_{1-6}$alkyloxycarbonyl; $C_{1-6}$alkyl substituted with one or two substituents selected from the group consisting of hydroxy, $C_{1-4}$alkyloxy, $C_{1-4}$alkyloxycarbonyl, mono- and di($C_{1-4}$alkyl)amino, aryl and Het$^2$; $C_{3-6}$alkenyl; $C_{3-6}$alkenyl substituted with aryl; piperidinyl; piperidinyl substituted with $C_{1-4}$alkyl or arylC$_{1-4}$alkyl; $C_{1-6}$alkylsulfonyl or arylsulfonyl;

aryl is phenyl or phenyl substituted with one, two or three substituents selected from halo, hydroxy, $C_{1-4}$alkyl, $C_{1-4}$alkyloxy, $C_{3-6}$cycloalkyl, trifluoromethyl, amino, nitro, carboxyl, $C_{1-4}$alkyloxycarbonyl and $C_{1-4}$alkylcarbonylamino;

Het$^1$ is pyridinyl; pyridinyl substituted with $C_{1-4}$alkyl; furanyl; furanyl substituted with $C_{1-4}$alkyl; thienyl; thienyl substituted with $C_{1-4}$alkylcarbonylamino; hydroxypyridinyl, hydroxypyridinyl substituted with $C_{1-4}$alkyl or $C_{1-4}$alkoxy-$C_{1-4}$alkyl; imidazolyl; imidazolyl substituted with $C_{1-4}$alkyl; thiazolyl; thiazolyl substituted with $C_{1-4}$alkyl; oxazolyl; oxazolyl substituted with $C_{1-4}$alkyl; isoquinolinyl; isoquinolinyl substituted with $C_{1-4}$alkyl; quinolinonyl, quinolinonyl substituted with $C_{1-4}$alkyl; morpholinyl; piperidinyl; piperidinyl substituted with $C_{1-4}$alkyl, $C_{1-4}$alkyloxycarbonyl or arylC$_{1-4}$alkyl; piperazinyl; piperazinyl substituted with $C_{1-4}$alkyl, $C_{1-4}$alkyloxycarbonyl or arylC$_{1-4}$alkyl; and Het$^2$ is morpholinyl; piperidinyl; piperidinyl substituted with $C_{1-4}$alkyl or arylC$_{1-4}$alkyl; piperazinyl; piperazinyl substituted with $C_{1-4}$alkyl or aryl$C_{1-4}$alkyl; pyridinyl; pyridinyl substituted with $C_{1-4}$alkyl; furanyl; furanyl substituted with $C_{1-4}$alkyl; thienyl or thienyl substituted with $C_{1-4}$alkyl or $C_{1-4}$alkylcarbonylamino.

Some of the compounds of formula (I) may also exist in their tautomeric forms. Such forms although not explicitly indicated in the above formula are intended to be included within the scope of the present invention. In particular, compounds of formula (I) wherein L is hydrogen may exist in their corresponding tautomeric form.

In $R^1$ and $R^2$, the saturated 5-, 6- or 7-membered heterocycles containing one or two heteroatoms selected from oxygen, sulfur or nitrogen may suitably be selected from heterocycles such as, for example, tetrahydrofuranyl, dioxolanyl, pyrrolidinyl, morpholinyl, piperidinyl, piperazinyl and tetrahydropyranyl. Said heterocyclic radicals are attached to the oxygen atom or the $C_{1-10}$alkyl radical by any carbon atom or, where appropriate, by a nitrogen atom.

Also in $R^1$ and $R^2$, the term 6,7-dihydro-5H-cyclopentapyridinyl, also named 6,7-dihydro-5H-pyrindinyl, is meant to represent 6,7-dihydro-5H-cyclopenta[b]pyridine or 6,7-dihydro-5H-cyclopenta[c]pyridinyl and may be attached to the remainder of the molecule by any of the aliphatic or aromatic carbon atoms.

As used herein the term halo is generic to fluoro, chloro, bromo and iodo; the term $C_{1-4}$alkyl is meant to include straight chained or branched saturated hydrocarbons having from 1 to 4 carbon atoms such as, for example, methyl, ethyl, 1-methylethyl, 1,1-dimethylethyl, propyl, 2-methylpropyl and butyl; the term $C_{1-6}$alkyl is meant to include $C_{1-4}$alkyl and the higher homologues thereof having 5 or 6 carbon atoms such as, for example, 2-methylbutyl, pentyl, hexyl and the like; the term $C_{1-6}$alkyl is meant to include $C_{2-6}$alkyl and the lower homologue thereof having 1 carbon atom such as, for example, methyl; $C_{1-10}$alkyl is meant to include $C_{1-6}$alkyl and the higher homologues thereof having from 7 to 10 carbon atoms such as, for example, heptyl, octyl, nonyl, decyl, 1-methylhexyl, 2-methylheptyl and the like; the term $C_{3-6}$alkenyl defines straight and branch chained hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl and the like; and the carbon atom of said $C_{3-6}$alkenyl being connected to a nitrogen atom preferably is saturated; the term $C_{3-6}$cycloalkyl is generic to cyclopropyl, cyclobutyl, cyclopentyl and cyclohexyl; the term $C_{3-7}$cycloalkyl is meant to include $C_{3-6}$cycloalkyl and cycloheptyl; the term $C_{1-4}$alkanediyl is meant to include straight chained and branched saturated bivalent hydrocarbon radicals having from 1 to 4 carbon atoms, such as, for example, methylene, 1,2-ethanediyl, 1,1-ethanediyl, 1,3-propanediyl, 1,2-propanediyl, 1,4-butanediyl, 2-methyl-1,3-propanediyl and the like.

As used in the foregoing definitions and hereinafter, halo$C_{1-4}$alkanediyl is defined as mono- or polyhalosubstituted $C_{1-4}$alkanediyl, in particular $C_{1-4}$alkanediyl substituted with one or more fluor atoms.

The pharmaceutically acceptable acid addition salts as mentioned hereinabove are meant to comprise the acid addition salt forms which can conveniently be obtained by treating the base form of the compounds of formula (I) with appropriate acids such as inorganic acids, for example, hydrohalic acid, e.g. hydrochloric or hydrobromic, sulfuric, nitric, phosphoric and the like acids; or organic acids, such as, for example, acetic, hydroxy-acetic, propanoic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely, said acid addition salt forms can be converted in the free base forms by treatment with an appropriate base.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt also comprises the hydrates and solvent addition forms which the compounds of formula (I) are able to form. Examples of such forms are e.g. hydrates, alcoholates and the like.

The N-oxide forms of the compounds of formula (I) are meant to comprise those compounds of formula (I) wherein one or several nitrogen atoms are oxidized to the so-called N-oxide.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration, and the =N—CN and substituted $C_{3-6}$alkenyl moieties may have the E- or Z-configuration.

Whenever used hereinafter, the term compounds of formula (I) is meant to include also the N-oxide forms, the pharmaceutically acceptable acid or base addition salts and all stereoisomeric forms.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically. The pure and mixed stereochemically isomeric forms of the compounds of formula (I) are intended to be embraced within the scope of the present invention.

An alternative manner of separating the enantiomeric forms of the compounds of formula (I) and intermediates involves liquid chromatography, in particular liquid chromatography using a chiral stationary phase.

A special group of compounds includes those compounds of formula (I) wherein $R^1$ and $R^2$ each independently are hydrogen; $C_{1-6}$alkyl; difluoromethyl; trifluoromethyl; $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen.

Interesting compounds are those compounds of formula (I) wherein $R^1$ and $R^2$ are each independently $C_{1-6}$alkyl; $C_{3-6}$cycloalkyl; difluoromethyl; a saturated 5-, 6- or 7-membered heterocycle containing one or two heteroatoms selected from oxygen, sulfur or nitrogen, which preferably is tetrahydrofuranyl; indanyl; or $C_{1-10}$alkyl substituted with aryl, indanyl, 6,7-dihydro-5H-cyclopentapyridinyl or $C_{3-6}$cycloalkyl.

Also interesting are those compounds of formula (I) wherein $R^5$ is hydrogen and $R^4$ is hydrogen, hydroxy or $C_{1-6}$alkyl, more in particular, $R^4$ is methyl.

Another interesting group are those compounds of formula (I) wherein L is hydrogen, $C_{1-6}$alkyloxycarbonyl, or $C_{1-6}$alkyl substituted with one or two phenyl rings.

Particular compounds are those compounds of formula (I) wherein $R^1$ is cyclopentyl, tetrahydrofuranyl, cyclopropylmethyl, 5-phenylpentyl, 2-indanylethyl, 6,7-dihydro-5H-cyclopenta[b]pyridinyl or indanyl; and $R^2$ is methyl or difluoromethyl.

Preferred compounds are those particular compounds wherein $R^3$, $R^5$, $R^6$, $R^{10}$, $R^{11}$ and L are hydrogen.

Most preferred are the following compounds:

[1-[2-[4-(difluoromethoxy)-3-[(tetrahydro-3-furanyl)oxy]phenyl]propyl]-1,3-dihydro-2H-imidazol-2-ylidene]cyanamide; and

[1-[2-[4-(methoxy)-3-[(1,3-dihydro-2H-inden-2-yl)oxy]phenyl]propyl]-1,3-dihydro-2H-imidazol-2-ylidene]cyanamide; their N-oxides, their stereochemically isomeric forms and their pharmaceutically acceptable additon salts.

Whenever used hereinafter, $R^1$ to $R^{11}$, Y, —A—B— and L are defined as under formula (I) unless otherwise indicated.

Compounds of formula (I) wherein —A—B— is a radical of formula (c-1) and L is hydrogen, said compounds being represented by formula (I-a-1), can conveniently be prepared by cyclization of an intermediate of formula (II) or a functional derivative thereof in the presence of a suitable acid such as, for example, hydrochloric acid.

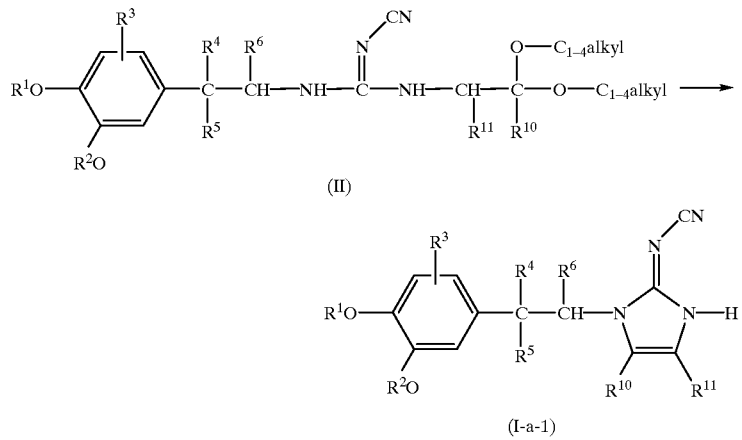

Said cyclization may be performed in a reaction inert solvent such as, for example, tetrahydrofuran or 1,4-dioxane or a mixture thereof. Stirring and heating may enhance the rate of the reaction.

In this and the following preparations, the reaction products may be isolated from the reaction medium and, if necessary, further purified according to methodologies generally known in the art such as, for example, extraction, crystallization, trituration and chromatography.

In particular, compounds of formula (I-a-1) wherein $R^5$ is hydroxy, said compounds being represented by formula (I-a-1-1), may be prepared by cyclization of an intermediate of formula (II-1) wherein P is hydrogen or, preferably, is a trimethylsilyl protecting group or a functional derivative thereof, in a manner analogous to the one described for the preparation of a compound of formula (I-a-1) from an intermediate of formula (II).

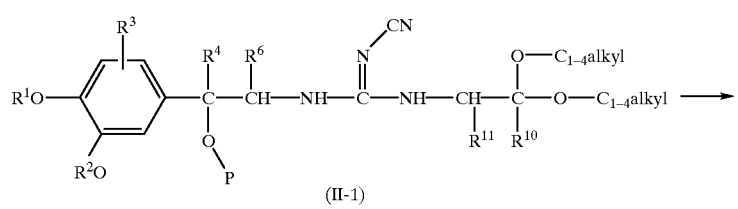

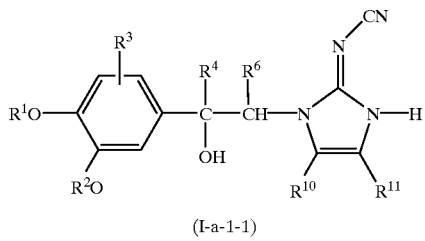

(I-a-1-1)

Compounds of formula (I) wherein —A—B— is a radical of formula (c-2) and L is hydrogen, said compounds being represented by formula (I-a-2), can be obtained by cyclization of an intermediate of formula (III) or a functional derivative thereof in the presence of a suitable reagent such as, for example, dimethyl cyanocarbonimidodithioate or diphenyl N-cyanocarbonimidate.

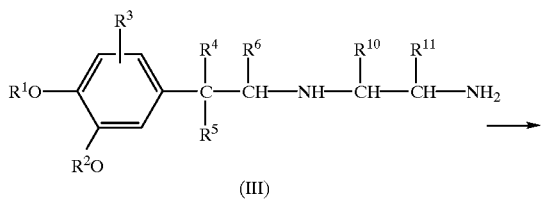

(III)

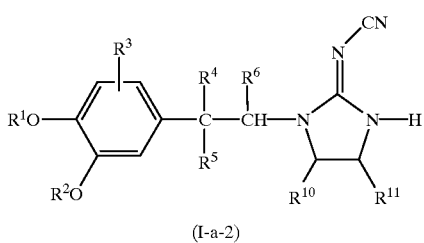

(I-a-2)

Alternatively, compounds of formula (I) may be prepared by reacting an organometallic intermediate of formula (IV), wherein M is an appropriate metal ion or metalcomplex ion such as, for example, $Li^+$, $(MgBr)^+$, $B(OH)_2{}^+$ or $Sn(CH_3)_3{}^+$, in a reaction-inert solvent with a suitable 2-cyanoiminoimidazole derivative of formula (V) wherein $W^1$ is a reactive leaving group such as, for example, a halogen. In case $R^4$ and $R^5$ are taken together and form a radical of formula (b-1), (b-2), (b-3) or (b-4), $W^1$ may also be a cyanide moiety provided that the intermediate of formula (IV) is a Grignard reagent.

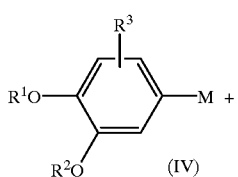

(IV)

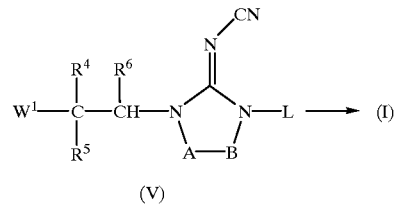

(V)

Said reaction may be performed in a reaction-inert solvent such as, for example, dimethoxyethane, tetrahydrofuran or diethylether. Stirring and heating may enhance the rate of the reaction. In case intermediates of formula (V), wherein L is replaced by a suitable protecting group, are used in said reaction, compounds of formula (I) wherein L is hydrogen, said compounds being represented by compounds of formula (I-a), may be obtained using art-known deprotection reactions.

The compounds of formula (I) can also be converted into each other following art-known procedures of functional group transformation.

For example, compounds of formula (I) wherein L is other than hydrogen, said compounds being represented by formula (I-b), may be prepared by reacting a compound of formula (I-a) with $L'$—$W^2$ (VI), wherein L' is the same as L defined under formula (I) but other than hydrogen and $W^2$ is a reactive leaving group such as, for example, a halogen atom.

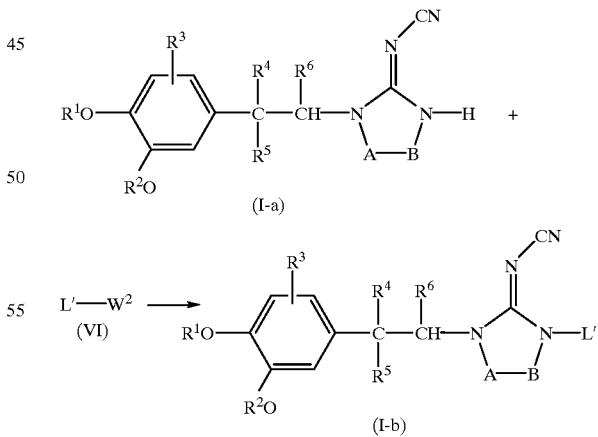

Also art-known addition reactions may be used to convert compounds of formula (I-a) into compounds of formula (I-b).

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Intermediates mentioned hereinabove may be prepared following art-known techniques.

In particular, intermediates of formula (II) may be prepared by first reacting an amine of formula (VII) with dimethyl cyanocarbonimidodithioate or diphenyl cyanocarbonimidate or a functional derivative thereof. Said reaction can conveniently be performed in a reaction inert solvent such as, for example, dichloromethane, benzene or toluene, optionally cooled on an ice-bath, and in the presence of a base such as, for example, N,N-diethylethanamine or sodiumbicarbonate. The thus obtained intermediate may be subsequently reacted with an intermediate of formula (VIII) or a functional derivative thereof, to form an intermediate of formula (II). Said reaction can conveniently be performed in a reaction inert solvent such as, for example, 1,4-dioxane, in the presence of a base such as, for example, N,N-diethylethanamine, and optionally in the presence of a catalyst such as, for example, N,N-dimethyl-pyridinamine. Stirring and elevated temperatures may enhance the rate of the reaction.

example, N,N-dimethylformamide. Subsequently, the cyanide moiety in the thus formed intermediate may be reduced using a suitable reducing agent such as, for example, lithium aluminium hydride or hydrogen in the presence of a catalyst such as, for example, Raney nickel, thus obtaining an intermediate of formula (III-1).

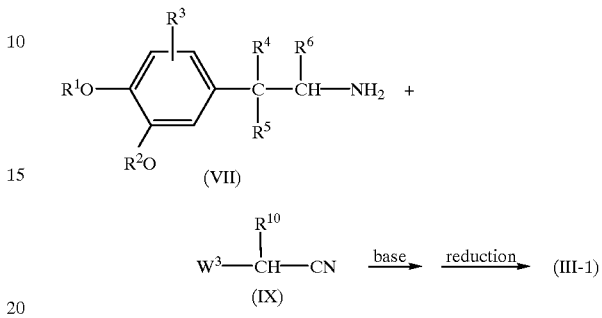

Some of the intermediates of formula (VII) are described in WO 92/00968, WO 93/15044 and WO 93/15045.

In particular, intermediates of formula (VII) may be prepared by reacting an intermediate of formula (X) wherein $W^4$ is a suitable leaving group such as, for example, a halogen with an intermediate of formula (XI) wherein M is an appropriate metal ion or metalcomplex ion such as, for example, $Li^+$ or $(MgBr)^+$, and P is a suitable protecting group such as, for example, (1,1-dimethylethyl)oxycarbonyl. The thus obtained protected intermediates of formula (VII) may subsequently be deprotected by art-known techniques such as, for example, acid hydrolysis.

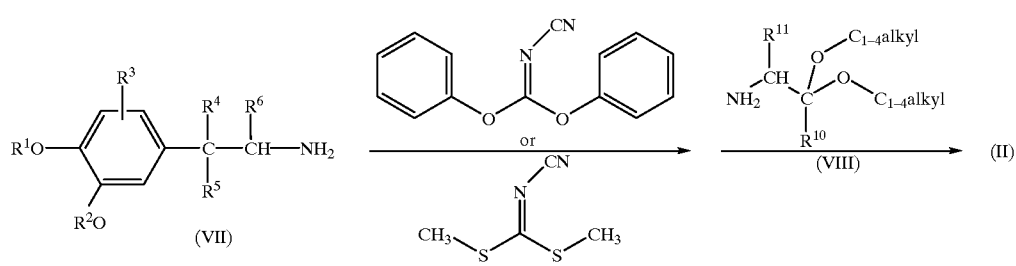

Alternatively, the above reaction may be performed in reverse order, i.e. first react an intermediate of formula (VIII) with dimethyl cyanocarbonimidodithioate or diphenyl cyanocarbonimidate or a functional derivative thereof, and subsequently react the thus formed intermediate with an amine of formula (VII).

Intermediates of formula (III) wherein $R^{11}$ is hydrogen, said intermediates being represented by formula (III-1), may be prepared by first reacting an amine of formula (VII) with a cyano derivative of formula (IX) wherein $W^3$ is an appropriate leaving group such as, for example, a halogen, in the presence of a base such as, for example, sodiumcarbonate, in a reaction-inert solvent such as, for Intermediates of formula (VII) wherein $R^6$ is hydrogen, said intermediates being represented by formula (VII-1), may be prepared by reducing the unsaturated carbon-nitrogen bond in the intermediates of formula (XII) with a suitable reducing agent such as, for example, borane-tetrahydrofuran-complex, lithium aluminium hydride, or hydrogen in the presence of a catalyst such as, for example, Raney nickel. The cyanide moiety in the intermediates of formula (XII) may also be replaced by a functional derivative thereof such as, for example, an oxime moiety.

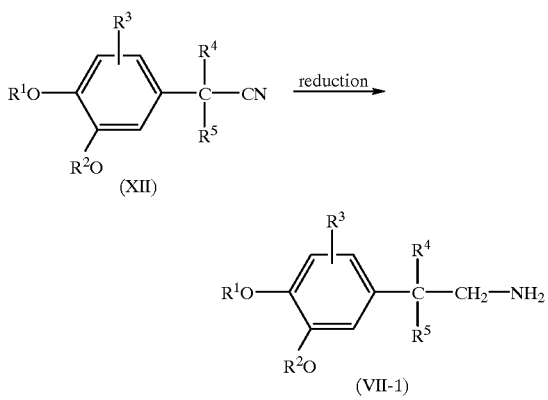

Some of the intermediates of formula (XII) are described in WO 92/00968, WO 93/15044 and WO 93/15045.

In particular, intermediates of formula (XII) wherein $R^5$ is a protected hydroxy group and $R^4$ is hydrogen, said intermediates being represented by formula (XII-1), can conveniently be prepared by reacting an aldehyde of formula (XIII) with a reagent of formula (XIV) or a functional derivative thereof wherein P is a protective group such as, for example, trimethylsilyl and the like. in a reaction-inert solvent such as, for example, dichloromethane, and in the presence of a catalytic amount of $ZnI_2$ or a functional derivative thereof. Said intermediates of formula (XII-1) may be further reacted as described hereinabove to finally form a compound of formula (I) wherein $R^5$ is hydroxy.

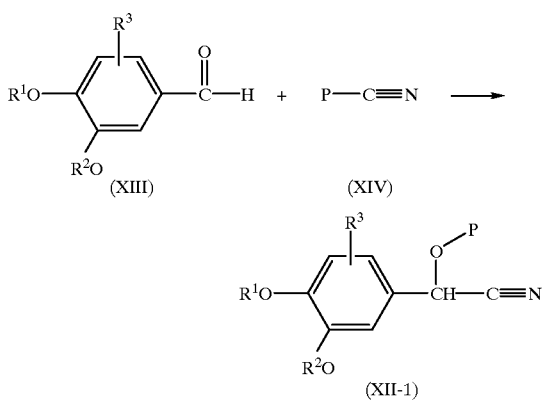

The aldehydes of formula (XIII) can conveniently be prepared analogous to the reaction procedure described by Mitsunobu Oyo in Synthesis, 1–28, 1981.

Some of the compounds of formula (I) and some of the intermediates in the present invention contain at least one asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers.

Pure stereochemically isomeric forms of the compounds of formula (I) may also be obtained from the pure stereochemically isomeric forms of the appropriate intermediates and starting materials, provided that the intervening reactions occur stereo-specifically. The pure and mixed stereochemically isomeric forms of the compounds of formula (I) are intended to be embraced within the scope of the present invention.

The compounds of formula (I), the N-oxide forms, pharmaceutically acceptable acid or base addition salts and the stereochemically isomeric forms thereof, are potent inhibitors of the phosphodiesterase (PDE) isoenzymes of family IV (cAMP-specific family).

cAMP (adenosine cyclic 3',5'-monophosphate) is a key second messenger, the concentration of which affects particular cell activities through activation of enzymes such as kinases. PDE IV is known to hydrolyse cAMP to its corresponding inactive 5'-monophosphate metabolite. Hence, inhibition of PDE IV leads to an elevation of cAMP levels in particular cells such as the respiratory smooth muscle cell and in a wide variety of inflammatory cells, i.e. certain lymphocytes, e.g. basophils, neutrophils and eosinophils, monocytes and mast-cells. A number of allergic, atopic and inflammatory diseases are deemed to be caused by higher-than-normal PDE IV concentrations which result in low cAMP levels and hypersensitivity of the thus affected cells for excitatory stimuli. (Examples of said hypersensitivity are for example, excessive histamine release from basophils and mast cells or excessive superoxide anion radical formation by eosinophils.) Hence, the present compounds having potent phosphodiesterase IV inhibitory properties are deemed useful agents in alleviating and/or curing allergic, atopic and inflammatory diseases. The functional effects of PDE IV inhibitors are e.g. respiratory smooth muscle relaxation, bronchodilation, platelet aggregation inhibition and inhibition of white blood cell mediator release. Examples of allergic diseases are bronchial asthma, cheilitis, conjunctivitis, contact dermatitis and eczema, irritable bowel disease, deshydroform eczema, urticaria, vasculitis, vulvitis; examples of atopic diseases are dermatitis and eczema, winterfeet, asthma, allergic rhinitis; and related afflictions are, for example, psoriasis and other hyperproliferative diseases.

The present invention thus also relates to compounds of formula (I) as defined hereinabove for use as a medicine, in particular for use as a medicine for treating atopic diseases or as an anti-asthmatic medicine. Thus the compounds of the present invention may be used for the manufacture of a medicament for treating atopic or asthmatic diseases, more in particular atopic dermatitis.

The PDE IV inhibitory activity of the compounds of formula (I) may be demonstrated in the test "Inhibition of recombinant human mononuclear lymphocyte (MNL) phosphodiesterase type IV B produced in insect cells with a baculovirus vector". Several in vivo and in vitro tests may be used to demonstrate the usefulness of the compounds of formula (I) in treating the described allergic, atopic and inflammatory diseases. Such tests are for instance, "Bronchoconstriction of the guinea pig trachea in vitro", "Bronchoconstriction of the guinea pig trachea in vivo" and the in vivo tests "Arachidonic acid induced pinnal inflammation in mice", "TPA induced ear inflammation in mice", and "Delayed type hypersensitivity in mice".

Further, the present compounds have only very low inhibitory activity on the phosphodiesterase isoenzymes of family III (cGMP-inhibited family). Inhibition of, in particular, PDE III leads to an elevation of cAMP in the cardiac muscle, thereby causing effects on the contractile force of the heart as well as on the relaxation of the heart. In the treatment of the described allergic, atopic and inflammatory diseases, cardiovascular effects clearly are undesired. Hence, as the present compounds inhibit PDE IV at much lower concentrations as they inhibit PDE III, their therapeutic use may be adjusted to avoid cardiovascular side-effects.

Art-known PDE IV inhibitors often cause adverse gastro-intestinal side effects. Most of the present compounds, however, have few effects on the gastro-intestinal tract, which may be demonstrated in the test "Gastric emptying of a caloric meal in rats".

The designation PDE III and IV as used herein refers to the classification by J. A. Beavo and D. H. Reifsnyder, TIPS Reviews, April 1990, pp. 150–155.

The compounds of the present invention also have cytokine inhibitory activity. A cytokine is any secreted polypeptide that affects the function of other cells by modulating interactions between cells in the immune or inflammatory response. Examples of cytokines are monokines and lymphokines and they may be produced by a wide variety of cells. For instance, a monokine is generally referred to as being produced and secreted by a mononuclear cell, such as a macrophage and/or monocyte but many other cells produce monokines, such as natural killer cells, fibroblasts, basophils, neutrophils, endothelial cells, brain astrocytes, bone marrow stromal cells, epideral keratinocytes, and β-lymphocytes. Lymphokines are generally referred to as being produced by lymphocyte cells. Examples of cytokines include Interleukin-1 (IL-1), Interleukin-2 (IL-2), Interleukin-6 (IL-6), Interleukin-8 (IL-8), alpha-Tumor Necrosis Factor (αTNF) and beta-Tumor Necrosis Factor (βTNF).

The cytokine specifically desired to be inhibited is αTNF. Excessive or unregulated TNF production is implicated in mediating or exacerbating a number of diseases including rheumatoid arthritis, rheumatoid spondylitis, osteoarthritis, gouty arthritis, and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft versus host reaction, allograft rejections, fever and myalgias due to infection, such as influenza, cachexia secondary to infection or malignancy, cachexia secondary to acquired immune deficiency syndrome (AIDS), AIDS, ARC (AIDS related complex), keloid formation, scar tissue formation, Crohn's disease, ulcerative colitis, or pyresis.

The cytokine inhibitory activity of the compounds of formula (I), such as the inhibition of αTNF production, may be demonstrated in the in vitro test "Cytokine production in human whole blood cultures".

In addition, the compounds of the present invention are expected to show no or little endocrinological side-effects. This may be evidenced by, for instance, the "Testosterone in vivo" test, the "In vitro inhibition of the aromatase activity"-test and the "In vivo inhibition of the aromatase activity"-test.

In view of their useful PDE IV and cytokine inhibiting properties, the subject compounds may be formulated into various pharmaceutical compositions for administration purposes comprising a pharmaceutically acceptable carrier, and as active ingredient a therapeutically effective amount of a compound of formula (I). To prepare the pharmaceutical compositions of this invention, a therapeutically effective amount of the particular compound, in base or acid addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for administration orally, rectally, topically, percutaneously, by inhalation or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellent such as nitrogen, carbon dioxide, a freon, or without a propellent such as a pump spray, drops, lotions, or a semisolid such as a thickened composition which can be applied by a swab. In particular, semisolid compositions such as salves, creams, gellies, ointments and the like will conveniently be used.

In order to enhance the solubility and/or the stability of the compounds of formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

It is especially advantageous to formulate the aforementioned pharmaceutical compositions in dosage unit form for ease of administration and uniformity of dosage. Dosage unit form refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

The present invention also relates to a method of treating warm-blooded animals suffering from disease states related to an abnormal enzymatic or catalytic activity of PDE IV, and/or disease states related to a physiologically detrimental excess of cytokines, in particular allergic, atopic and inflammatory diseases, more in particular asthmatic and atopic diseases, most particular atopic dermatitis. Said method comprises the administration of a therapeutically effective amount of a compound of formula (I) or a N-oxide form, a pharmaceutically acceptable acid or base addition salt or a stereochemically isomeric form thereof in admixture with a pharmaceutical carrier.

In general it is contemplated that an effective daily amount would be from 0.01 mg/kg to 10 mg/kg body weight. It is evident that said effective daily amount may be lowered or increased depending on the response of the treated subject and/or depending on the evaluation of the physician prescribing the compounds of the instant invention. The effective daily amount range mentioned hereinabove are therefore guidelines only and are not intended to limit the scope or use of the invention to any extent.

The following examples are intended to illustrate and not to limit the scope of the present invention.

Experimental Part

Of some compounds of formula (I) the absolute stereochemical configuration was not experimentally determined. In those cases the stereochemically isomeric form which was first isolated is designated as "A" and the second as "B", without further reference to the actual stereochemical configuration.

Hereinafter, "THF" means tetrahydrofuran, "RT" means room temperature, "DMF" means N,N-dimethylformamide and "DIPE" means diisopropylether.

A. Preparation of the Intermediate Compounds

Example A.1 a) Potassium carbonate (0.0569 mol) was added dropwise to a mixture of 4-difluoromethoxy-3-hydroxybenzaldehyde (0.053 mol) and (tetrahydro-3-furanol)-4-methylbenzenesulfonate (15.35 g) in DMF (100 ml) under $N_2$ flow. The reaction mixture was stirred for 4 hours at 100° C. The mixture was cooled and a solution of (tetrahydro-3-furanol)-4-methylbenzenesulfonate (3.98 g) in DMF (40 ml) was added dropwise and the reaction mixture was stirred for 3 hours at 100° C., then overnight at RT. The solvent was evaporated and the residue was washed in a saturated aqueous $Na_2CO_3$ solution, then extracted with DIPE. The separated organic layer was dried, filtered, and the solvent was evaporated, yielding 17.77 g of (±)-4-(difluoromethoxy)-3-[(tetrahydro-3-furanyl)oxy] benzaldehyde (intermediate 1).

b) A sodium borohydride solution (0.0177 mol) was added portionwise to a solution of intermediate 1 (0.0532 mol) in methanol (100 ml), and the reaction mixture was stirred for 1 hour at RT. The solvent was evaporated, the residue was washed with water, and extracted with $CH_2Cl_2$. The separated organic layer was dried, filtered, and the solvent was evaporated. The residue was purified by open column chromatography over silica gel (eluent: $CH_2Cl_2$/2-propanone 96/4 and 90/10; $CH_2Cl_2/CH_3OH$ 96/4). The pure fractions were collected and the solvent was evaporated, yielding 11.3 g (81%) of (±)-4-(difluoromethoxy)-3-[(tetrahydro-3-furanyl)oxy]benzenemethanol (intermediate 2).

c) A solution of intermediate 2 (0.039 mol) in toluene (45 ml) was added dropwise to a mixture of $SOCl_2$ (0.059 mol) and DMF (0.0019 mol) in toluene (75 ml), stirred at 40° C. The resulting reaction mixture was stirred at 40° C., until HCl-gas evolution had stopped. The solvent was evaporated and the residue was washed with a saturated aqueous $NaHCO_3$ solution, and extracted with $CH_2Cl_2$. The separated organic layer was dried, filtered, and the solvent evaporated, yielding 10.59 g (96%) of (±)-4-(difluoromethoxy)-3-[(tetrahydro-3-furanyl)oxy] benzenemethanol (intermediate 3).

d) A mixture of KCN (0.076 mol) in $H_2O$ (4 ml), heated to 80° C., was added dropwise to a mixture of intermediate 3 (0.038 mol) in DMF (82.4 ml), stirred at 60° C. The resulting reaction mixture was stirred for 30 minutes at 60° C. The reaction mixture was cooled, washed with water, extracted with DIPE. The extract was dried, filtered, and the filtrate was evaporated, yielding 8.23 g (80%) of (±)-4-(difluoromethoxy)-3-[(tetrahydro-3-furanyl)oxy] benzeneacetonitrile (intermediate 4).

In a similar way, there were prepared:
3-(cyclopropylmethoxy)-4-methoxybenzeneacetonitrile (intermediate 5);
3-[(1,3-dihydro-2H-inden-2-yl)oxy]-4-methoxybenzeneacetonitrile (intermediate 6);
(±)-4-methoxy-3-[(tetrahydro-3-furanyl)oxy] benzeneacetonitrile (intermediate 7);
4-methoxy-3-[(5-phenylpentyl)oxy]benzeneacetonitrile (intermediate 8);
4-(difluoromethoxy)-3-[(5-phenylpentyl)oxy] benzeneacetonitrile(intermediate 23).

Example A.2 a) N-(1-methylethyl)-2-propanamine lithium salt (0.0325 mol; 1 M in THF) was added dropwise and under $N_2$ flow to intermediate 4 (0.0309 mol) in THF (70 ml), cooled to −78° C. The mixture was stirred for 30 minutes at −78° C. Iodomethane iodide (0.034 mol) was added dropwise and the reaction mixture was stirred for 2 hours at RT. The mixture was quenched with a saturated aqueous $NH_4Cl$ solution, and extracted with ethylacetate. The separated organic layer was dried, filtered, and the solvent was evaporated. The residue was purified by short open column chromatography over silica gel (eluent: $CH_2Cl_2$), then by HPLC over silica gel (eluent: hexane/ethylacetate 3/2). The pure fractions were collected and the solvent, yielding 4.64 g (53%) of (±)-4-(difluoromethoxy)-alpha-methyl-3-[(tetrahydro-3-furanyl)oxy]benzeneacetonitrile (intermediate 9).

b) A mixture of intermediate 9 (0.0129 mol) in $CH_3OH/NH_3$ (100 ml) was hydrogenated at RT with Raney Nickel (3 g) as a catalyst. After uptake of $H_2$, the catalyst was filtered off and the filtrate was evaporated, yielding 3.66 g (98%) of (±)-4-(difluoromethoxy)-β-methyl-3-[(tetrahydro-3-furanyl)oxy]benzeneethanamine (intermediate 10).

c) A mixture of intermediate 10 (0.0158 mol) and diphenyl N-cyano-carbonimidate (0.0158 mol) in ethanol (60 ml)

was stirred overnight at RT. The solvent was evaporated and the residue was purified by open column chromatography over silica gel (eluent: hexane/ethylacetate 3/2 and $CH_2Cl_2$/$CH_3OH$ 96/4, 90/10 and 85/5). The pure fractions were collected and the solvent was evaporated, yielding 5.11 g (74%) of (±)-phenyl N-cyano-N-[2-[4-(difluoromethoxy)-3-[(tetrahydro-3-furanyl)oxy] phenyl]propyl]carbamimidate (intermediate 11).

d) A mixture of 2,2-dimethoxyethanamine (0.0129 mol), N,N-diethylethanamine (0.023 mol) and N,N-dimethyl-4-pyridinamine (0.0059 mol) in 1,4-dioxane (30 ml) was added to a solution of intermediate 11 (0.0117 mol) in 1,4-dioxane (10 ml), stirred at RT. The reaction mixture was stirred and refluxed overnight. The solvent was evaporated and the residue was washed with water and 1 N NaOH, then extracted with $CH_2Cl_2$. The separated organic layer was dried, filtered, and the solvent was evaporated. The residue was purified by open column chromatography over silica gel (eluent: $CH_2Cl_2$/$CH_3OH$ 96/4). The pure fractions were collected and the solvent was evaporated, yielding 4.97 g (95%) of (±)-N"-cyano-N-[2-[4-(difluoromethoxy)-3-[(tetrahydro-3-furanyl)oxy]phenyl]propyl]-N'-(2,2-dimethoxyethyl)guanidine (intermediate 12).

In a similar way, there were prepared:

(±)-N"-cyano-N-[2-[3-(cyclopentyloxy)-4-methoxyphenyl]propyl]-N'-(2,2-dimethoxyethyl)guanidine (intermediate 13);

(±)-N"-cyano-N-[2-[3-(cyclopentyloxy)-4-(difluoromethoxy)phenyl]propyl]-N'-(2,2-dimethoxyethyl)guanidine (intermediate 14);

N"-cyano-N-[2-[3-(cyclopentyloxy)-4-(difluoromethoxy)phenyl]ethyl]-N'-(2,2-dimethoxyethyl)guanidine (intermediate 15);

(±)-N"-cyano-N-[2-[3-(cyclopropylmethoxy)-4-(difluoromethoxy)phenyl]propyl]-N'-(2,2-dimethoxyethyl)guanidine (intermediate 16);

(±)-N"-cyano-N-[2-[3-[(1,3-dihydro-2H-inden-2-yl)oxy]-4-methoxyphenyl]propyl]-N'-(2,2-dimethoxyethyl)guanidine (intermediate 17);

(+)-N"-cyano-N-[2-[3-(cyclopropylmethoxy)-4-methoxyphenyl]propyl]-N'-(2,2-dimethoxyethyl)guanidine (intermediate 18);

(±)-N"-cyano-N-(2,2-dimethoxyethyl)-N'-[2-[4-methoxy-3-[(5-phenylpentyl)oxy] phenyl]propyl]guanidine (intermediate 19);

(±)-N"-cyano-N-(2,2-dimethoxyethyl)-N'-[2-[4-methoxy-3-[(tetrahydro-3-furanyl)oxy]phenyl]propyl]guanidine (intermediate 20);

N"-cyano-N'-(2,2-dimethoxyethyl)-N-[2-[4-(difluoromethoxy)-3-[(5-phenylpentyl)oxy]phenyl]propyl]guanidine(intermediate 24);

N"-cyano-N'-[2-[3-[(2,3-dihydro-1H-inden-2-yl)oxy]-4-methoxyphenyl]ethyl]-N-(2,2-dimethoxyethyl)guanidine(intermediate 25)

(±)-N"-cyano-N-[2-[3-[2-(2,3-dihydro-1H-inden-2-yl)ethoxy]-4-methoxyphenyl] propyl]-N'-(2,2-dimethoxyethyl)guanidine (intermediate 27);

(±)-N"-cyano-N-[2-[3-[(2,3-dihydro-1H-inden-2-yl)oxy]-4-methoxyphenyl]-2-[(tetra-hydro-2H-pyran-2-yl)oxy]ethyl]-N'-(2,2-dimethoxyethyl)guanidine (intermediate 28).

Example A.3 a) A mixture of (±)-3-(cyclopentyloxy)-4-methoxy-β-methylbenzeneethanamine (0.029 mol), chloroacetonitrile (0.0146 mol) and sodium carbonate (0.0219 mol) in DMF (200 ml) was stirred for 5 hours at 60° C. The reaction mixture was filtered and the filtrate was evaporated. The residue was washed with water, then extracted with 2-methoxy-2-methylpropane. The separated organic layer was dried, filtered, and the solvent was evaporated. The residue was purified by open column chromatography over silica gel (eluent: $CH_2Cl_2$; $CH_2Cl_2$/2-propanone 96/4, and 90/10; then, $CH_2Cl_2$/$CH_3OH$ 80/20). The pure fractions were collected and the solvent was evaporated, yielding 3.24 g (77%) of (±)-[[2-[3-(cyclopentyloxy)-4-methoxyphenyl] propyl]amino]acetonitrile (intermediate 21).

b) A mixture of intermediate 21 (0.0117 mol) in $NH_3$/$CH_3OH$ (60 ml) was hydrogenated at RT with Raney Nickel (2 g) as a catalyst. After uptake of $H_2$, the catalyst was filtered off and the filtrate was evaporated. The residue was treated with a 10% aqueous HCl solution, and this mixture was extracted with ethylacetate. The layers were separated. The aqueous phase was basified, then extracted with ethylacetate. The separated organic layer was dried, filtered, and the solvent was evaporated, yielding 2.71 g (75%) of (±)-N-[2-[3-(cyclopentyloxy)-4-methoxyphenyl]propyl]-1,2-ethanediamine (intermediate 22).

Example A.4 a) A mixture of 6,7-dihydro-5H-cyclopenta[b]pyridin-7-ol (0.03544 mol), 3-hydroxy-4-methoxybenzaldehyde (0.0322 mol) and triphenylphosphine (0.0322 mol) in THF (100 ml) was stirred at 5° C. under $N_2$ atmosphere. Bis(1-methylethyl) diazenedicarboxylate (0.0322 mol) was added dropwise and the resulting reaction mixture was stirred for 12 hours at RT. The solvent was evaporated. $CH_2Cl_2$ was added to the residue. The mixture was washed with water, dried, filtered and the solvent was evaporated. The residue was purified over silica gel on a glass filter (eluent: $CH_2Cl_2$/$CH_3OH$ from 100/0 to 98.5/1.5). The desired fractions were collected and the solvent was evaporated. The residue was dissolved in 2-propanol and converted into the hydrochloric acid salt (1:1) with HCl/2-propanol. The solvent was evaporated. The residue was stirred in DIPE, filtered off and dried, yielding 8.2 g (83%) of 3-[(5,6-dihydro-7H-pyrindin-7-yl)oxy]-4-methoxybenzaldehyde hydrochloride (intermediate 34).

b) A solution of trimethylsilanecarbonitrile, (0.1472 mol) in $CH_2Cl_2$ (60 ml) was added dropwise to a mixture of 3-[(2,3-dihydro-1H-inden-2-yl)oxy]-4-methoxybenzaldehyde (0.1227 mol) and Zinc iodide (0.0061 mol) in $CH_2Cl_2$ (240 ml). The resulting reaction mixture was stirred for one hour at RT. The crude reaction mixture was washed with water and brine, then extracted with $CH_2Cl_2$. The separated organic layer was dried, filtered, and the solvent was evaporated. The residue was crystallized from DIPE. The precipitate was filtered off and dried, yielding 37.39 g (83%) of (±)-3-[(2,3-dihydro-1H-inden-2-yl)oxy]-4-methoxy-α-[(trimethylsilyl)oxy]benzeneacetonitrile (intermediate 29).

c) Intermediate 29 (0.1116 mol) was dissolved in methanol. HCl (3 N, 25 ml) was added. The mixture was stirred for 5 minutes. Most of the solvent was evaporated and $CH_2Cl_2$ was added. The organic layer was separated, washed with a saturated aqueous $NaHCO_3$ solution, dried, filtered and the solvent was evaporated. The residue was dissolved in $CH_2Cl_2$ (350 ml). 3,4-dihydro-2H-pyrane (0.2231 mol) and 4-methylbenzenesulfonic acid (catalytic quantity) were added and the resulting reaction mixture was stirred overnight at RT. The mixture was washed with a saturated aqueous $NaHCO_3$ solution, dried, filtered and the solvent was evaporated. The residue was purified by short open column chromatography over silica gel (eluent: hexanes/ ethylacetate 9/1, then 8/2). The desired fractions were collected and the solvent was evaporated, yielding: 28.01 g (66%) of (±)-3-[(2,3-dihydro-1H-inden-2-yl)oxy]-4-methoxy-α-[(tetrahydro-2H-pyran-2-yl)oxy]benzeneacetonitrile (intermediate 30).

Example A.5 a) A solution of bis(1,1-dimethylethyl) dicarbonoate (1.268 mol) in $CH_2Cl_2$ (1800 ml) was added dropwise to a solution of (±)-3-[(2,3-dihydro-1H-inden-2-yl)oxy]-4-methoxy-β-methylbenzeneethanamine (1.208 mol) in C (1800 ml). The mixture was stirred at RT for 2 hours. The solvent was evaporated. The residue was stirred in hexane, filtered off and dried, yielding 420 g of (±)-1,1-dimethylethyl [2-[3-[(2,3-dihydro-1H-inden-2-yl)oxy]-4-methoxyphenyl]propyl]carbamate (intermediate 31).

b) Intermediate 31 (1.056 mol) was purified and separated by chiral column chromatography over Chiralpack AD (eluent: hexane/$C_2H_5OH$/$CH_3OH$ 90/10/10). The desired fraction group was collected and the solvent was evaporated, yielding 268 g 1,1-dimethylethyl B-[2-[3-[(2,3-dihydro-1H-inden-2-yl)oxy]-4-methoxyphenyl]-propyl]-carbamate (intermediate 32).

c) A mixture of intermediate 32 (0.67 mol) in HCl (670 ml; 6N) and methanol (2700 ml) was stirred and refluxed for 90 minutes. The solvent was evaporated. The residue was taken up in $CH_2Cl_2$. The organic solution was washed with $H_2O$ (1000 ml) and a saturated $NaHCO_3$ solution. The organic layer was separated, dried, filtered and the solvent was evaporated, yielding 158g (99%) of (B)-3-[(2,3-dihydro-1H-inden-2-yl)oxy]-4-methoxy-β-methylbenzeneethanamine (intermediate 33). Intermediate 33 was further reacted according to the procedure described in example A.2.b to A.2.d to form (B)-N"-cyano-N-[2-[3-[(2,3-dihydro-1H-inden-2-yl)oxy]-4-methoxyphenyl]propyl]-N'-(2,2-dimethoxyethyl)guanidine (intermediate 26).

B. Preparation of the Compounds of Formula (I)

Example B.1

A mixture of intermediate 22 (0.0068 mol) and dimethyl cyanocarbonimidodithioate (0.0068 mol) in ethanol (20 ml) was stirred and refluxed for 2 days. The solvent was evaporated and the residue was first purified by short open column chromatography over silica gel (eluent: $CH_2Cl_2$, $CH_2Cl_2$/$CH_3OH$ 96/4 and 90/10), then twice by HPLC (1 eluent: $CH_2Cl_2$/$CH_3OH$ 90/10 and 2. Eluent: $CH_2Cl_2$/$CH_3OH$ 96/4). The pure fractions were collected and the solvent was evaporated, yielding 0.3 g (13%) of (±)-[1-[2-[3-(cyclopentyloxy)-4-methoxyphenyl]propyl]-2-imidazolidinylidene] cyanamide (compound 1).

Example B.2

HCl 0.5 N (0.0162 mol) was added dropwise to a solution of intermediate 12 (0.0108 mol) in 1,4-dioxane (20 ml), stirred and cooled in an ice-bath. The reaction mixture was stirred for 2 days at RT. (As an alternative, 1,4-dioxane may be replaced by THF and the reaction mixture may be refluxed for 1 hour instead of stirring 2 days at RT). The reaction mixture was treated with water, alkalized with a dilute NaOH solution, then extracted with ethylacetate. The separated organic layer was dried, filtered, and the solvent was evaporated. The residue was purified by open column chromatography over silica gel (eluent: $CH_2C_2$/2-propanone 96/4; $CH_2Cl_2$/$CH_3OH$ 96/4) and twice by HPLC over silica gel (1. Eluent: $CH_2Cl_2$/$CH_3OH$ 96/4 and 2. Eluent: $CH_2Cl_2$/$CH_3OH$ 97/3). The pure fractions were collected and the solvent was evaporated, yielding 0.64 g (15%) of (±)-[1-[2-[4-(difluoromethoxy)-3-[(tetrahydro-3-furanyl)oxy]phenyl]-propyl]-1,3-dihydro-2H-imidazol-2-ylidene] cyanamide (compound 2; mp. 67.8° C.).

Example B.3 a) Compound 7 (0.00644 mol) was separated into its enantiomers by chiral column chromatography over Chiralpak AD (20 $\mu$m, 250 g, 5 cm, flow: 60 ml/min; eluent: hexane/ethanol/methanol 80/15/5). Two desired fraction groups were collected. The solvent of the first (A)-fraction group was evaporated. The residue was stirred in DIPE, filtered off, washed with DIPE, then dried. The residue was further purified by column chromatography over Kromasil silica gel (200 g, 5 $\mu$m, eluent: $CH_2Cl_2$/$CH_3OH$ 100/0, after 30 minutes, 90/10). The pure fractions were collected and the solvent was evaporated. The residue was stirred in DIPE, filtered off, washed with DIPE, then dried, yielding 0.39 g (50%) of (+)-(A)-[1-[2-[3-[(2,3-dihydro-1H-inden-2-yl)oxy]-4-methoxy-phenyl]-propyl]-1H-imidazol-2-yl]cyanamide; $[\alpha]_D^{20}$=+95.46° (c=0.1% in $CH_3OH$) (compound 16). The solvent of the second (B)-fraction group was evaporated. The residue was stirred in DIPE, filtered off, washed with DIPE, then dried. The residue was purified by column chromatography over Kromasil silica gel (200 g, 5 $\mu$m, eluent: $CH_2Cl_2$/$CH_3OH$ 100/0, after 30 minutes, 90/10). The pure fractions were collected and the solvent was evaporated. The residue was stirred in DIPE, filtered off, washed with DIPE, then dried, yielding 0.5 g (90%) of (−)-(B)-[1-[2-[3-[(2,3-dihydro-1H-inden-2-yl)oxy]-4-methoxy-phenyl]propyl]-1H-imidazol-2-yl]cyanamide; $[\alpha]_D^{20}$=−109.04° (c=0.1% in $CH_3OH$) (compound 17).

b) A mixture of compound 17 (0.0026 mol) in DMF (40 ml) was stirred at 0° C. Sodium hydride (0.0028 mol; 60%) was added and the mixture was stirred for 30 minutes at 0° C. and for 30 minutes at RT. A solution of bromomethylbenzene (0.0028 mol) in DMF (10 ml) was added dropwise and the resulting reaction mixture was stirred for 3 hours at RT. The solvent was evaporated, toluene was added and azeotroped on the rotary evaporator. The residue was taken up into $CH_2Cl_2$. Water was added. The organic layer was separated, dried, filtered and the solvent was evaporated. The residue was purified by short column chromatography over silica gel (eluent: $CH_2Cl_2$/$CH_3OH$ 98/2). The desired fractions were collected and thesolvent was evaporated, yielding 0.7 g (63%) of (B)-[1-[2-[3-[(2,3-dihydro-1H-inden-2-yl)oxy]-4-methoxy-phenyl]propyl]-3-phenylmethyl-1H-imidazol-2-yl]cyanamide (compound 23).

Example B.4

HCl (0.0268 mol; 0.5N) was added to a solution of intermediate 28 (0.0179 mol) in THF (250 ml), stirred and cooled on an ice-bath. The reaction mixture was stirred and refluxed for 1.5 hours, then cooled on an ice-bath. The mixture was partitioned between water and ethylacetate, and alkalized with solid $Na_2CO_3$. The organic layer was separated, dried, filtered, and the solvent was evaporated. The residue was purified by short open column chromatography over silica gel (eluent: $CH_2Cl_2$/$CH_3OH$ 97/3, then 95/5). The desired pure fraction group was collected. The solvent was evaporated and the residue was crystallized from $CH_3CN$, filtered off and dried, yielding (35%) of (±)-[1-[2-[3-[(2,3-dihydro-1H-inden-2-yl)oxy]-4-methoxyphenyl]-2-hydroxyethyl]-1,3-dihydro-2H-imidazol-2-ylidine]cyanamide (compound 21).

Table 1 lists compounds of formula (I) that were prepared according to one of the above examples.

TABLE 1

| Co. No. | Ex. No. | R¹ | R² | R⁴ | L | —A—B— | Physical data mp in ° C. |
|---|---|---|---|---|---|---|---|
| 1 | B.1 | cyclopentyl | $CH_3$ | $CH_3$ | H | —$CH_2$—$CH_2$— | (E + Z) |
| 2 | B.2 | 3-tetrahydrofuranyl | $CHF_2$ | $CH_3$ | H | —CH=CH— | 67.8° C. |
| 3 | B.2 | cyclopentyl | $CH_3$ | $CH_3$ | H | —CH=CH— | 101.3° C. |
| 4 | B.2 | cyclopentyl | $CHF_2$ | $CH_3$ | H | —CH=CH— | 133° C. |
| 5 | B.2 | cyclopentyl | $CHF_2$ | H | H | —CH=CH— | 158.9° C. |
| 6 | B.2 | cyclopropylmethyl | $CHF_2$ | $CH_3$ | H | —CH=CH— | liquid |
| 7 | B.2 | 2-indanyl | $CH_3$ | $CH_3$ | H | —CH=CH— | 87.5° C. |
| 8 | B.2 | cyclopropylmethyl | $CH_3$ | $CH_3$ | H | —CH=CH— | 66.2° C. |
| 9 | B.2 | phenylpentyl | $CH_3$ | $CH_3$ | H | —CH=CH— | — |
| 10 | B.2 | 3-tetrahydrofuranyl | $CH_3$ | $CH_3$ | H | —CH=CH— | 73.4° C. |
| 11 | B.2 | phenylpentyl | $CHF_2$ | $CH_3$ | H | —CH=CH— | — |
| 12 | B.3 | cyclopentyl | $CH_3$ | $CH_3$ | H | —CH=CH— | (A) |
| 13 | B.3 | cyclopentyl | $CH_3$ | $CH_3$ | H | —CH=CH— | (B) |
| 14 | B.3 | cyclopropylmethyl | $CH_3$ | $CH_3$ | H | —CH=CH— | (A) |
| 15 | B.3 | cyclopropylmethyl | $CH_3$ | $CH_3$ | H | —CH=CH— | (B) |
| 16 | B.3 | 2-indanyl | $CH_3$ | $CH_3$ | H | —CH=CH— | (A) |
| 17 | B.2 or B.3 | 2-indanyl | $CH_3$ | $CH_3$ | H | —CH=CH— | (B); 138.7° C. |
| 18 | B.3 | phenylpentyl | $CH_3$ | $CH_3$ | H | —CH=CH— | (A) |
| 19 | B.3 | phenylpentyl | $CH_3$ | $CH_3$ | H | —CH=CH— | (B) |
| 20 | B.2 | 2-indanyl | $CH_3$ | H | H | —CH=CH— | — |
| 21 | B.4 | 2-indanyl | $CH_3$ | OH | H | —CH=CH— | mp. 179.9° C. |
| 22 | B.2 | 2-indanyl-$(CH_2)_2$— | $CH_3$ | $CH_3$ | H | —CH=CH— | mp. 115.3° C. |
| 23 | B.3b | 2-indanyl | $CH_3$ | $CH_3$ | phenylmethyl | —CH=CH— | (B) |
| 24 | B.3b | 2-indanyl | $CH_3$ | $CH_3$ | C(=O)$OC_2H_5$ | —CH=CH— | (B) |

TABLE 1-continued

![Structure with R2O, R1O on phenyl ring, CH(R4)CH2-N in 5-membered ring with N-CN, N-L, A-B]

| Co. No. | Ex. No. | R¹ | R² | R⁴ | L | —A—B— | Physical data mp in ° C. |
|---|---|---|---|---|---|---|---|
| 25 | B.3b | 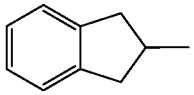 | CH₃ | CH₃ | diphenylmethyl | —CH=CH— | (B) |
| 26 | B.2 | 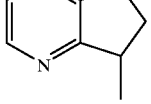 | CH₃ | H | H | —CH=CH— | — |

C. Pharmacological Example

Example C.1: Inhibition of Recombinant Human Mononuclear Lymphocyte (MNL) Phosphodiesterase Type IV B Produced in Insect Cells with a Baculovirus Vector The alleviating and/or curing effect of the instant compounds on allergic and atopic diseases was assessed by an in vitro assay system to detect an inhibiting effect on the recombinant human MNL phosphodiesterase type IV B.

Seventy-two hours after infection with recombinant baculovirus, the insect cells were harvested and pelleted at 500 g for 5 minutes. The cells were lysed in 10 ml lysis-buffer consisting of 20 mM Tris, 10 mM EGTA, 2 mM Na₂EDTA, 1% Triton-X-100, 1 mM Na₃VO₄, 10 mM NaF, 2 μg/ml of leupeptine, pepstatine and aprotinine, 0.3 μg/ml benzamidine and 100 μg/ml TPCK pH 7.5. After 5 minutes on ice, solubilized cells were centrifuged at 4000 rpm for 15 minutes at 4° C. The resulting supernatant was filtered through a 0.45 μm filter (Millipore) and brought to TBS buffer (50 mM Tris, 150 mM NaCl pH 7.4).

The supernatant containing phosphodiesterase (PDE) type IV B, was subsequently loaded onto a 5 ml anti-FLAG-M₂ affinity gel column, previously activated with 5 ml 100 mM glycine pH 3.5 and equilibrated with 20 ml 50 mM Tris, 150 mM NaCl pH 7.4. After washing the column with equilibration buffer, PDE IV was eluted in 1.5 ml fractions containing 37.5 μl 1M Tris pH 8. The fractions were dialyzed overnight against 20 mM Tris, 2 mM Na₂EDTA and 400 mM NaCl pH 7.5 and tested for PDE IV activity. Indentification was done on SDS PAGE and Western Blot (anti-FLAG-M₂). Active fractions were pooled, brought to 10% glycerol and stored at −70° C.

The incubation mixture (pH 8) (200 μl) contained 20 mM Tris, 10 mM magnesium sulphate, 0.8 μM ³H-cAMP (310 mCi/mmole) and the phosphodiesterase type IV, the amount depending on the enzymatic activity. A protein concentration was chosen that showed a linear increase of phosphodiesterase activity during an incubation period of maximum 10 minutes at 37° C. and where less than 10% of the initial substrate was hydrolyzed. When the effect of different compounds on phosphodiesterase activity was tested, the medium without cAMP was incubated with the compound (s) or its carrier (DMSO-1% final concentration) for 5 minutes. The enzymatic reaction was started by addition of ³H-cAMP and stopped 10 minutes later after transferring the microtiter-plate in a waterbath at 100° C. for 5 minutes. After cooling to room temperature, alkaline phosphatase (0.25 μg/ml) was added and the mixture was incubated at 37° C. for 20 min. 100 μl of the mixture was subsequently applied to a GF-B filter-microtiter-plate (Millipore) filled with 300 μl DEAE-Sephadex-A25 suspension. The plate was washed 3 times with 75 μl 20 mM Tris pH 7.5 and the filtrates were collected for counting in the Packard Top Count scintillation counter.

The inhibiting effect of the present compounds on recombinant human MNL phosphodiesterase PDE IV B was measured at different concentrations of the instant compounds. The IC₅₀ values (expressed in M) were calculated graphically from the thus obtained inhibition values and are listed in Table 2.

TABLE 2

| Comp. No. | IC₅₀ (in 10⁻⁸ M) |
|---|---|
| 1 | 33.0 |
| 2 | 10.0 |
| 3 | 3.00 |
| 4 | 1.53 |
| 5 | 2.66 |
| 6 | 2.24 |
| 7 | 1.90 |
| 8 | 5.65 |
| 9 | 3.61 |
| 10 | 19.6 |
| 11 | 3.27 |
| 12 | 2.19 |
| 13 | 2.22 |
| 14 | 2.72 |
| 15 | 3.35 |
| 16 | 1.80 |
| 17 | 3.00 |
| 18 | 4.09 |
| 19 | 3.75 |
| 20 | 7.65 |

D. Composition Examples

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

Example D. 1: Film-Coated Tablets

Preparation of Tablet Core

A mixture of 100 g of the A.I., 570 g lactose and 200 g starch was mixed well and thereafter humidified with a solution of 5 g sodium dodecyl sulfate and 10 g polyvinylpyrrolidone in about 200 ml of water. The wet powder mixture was sieved, dried and sieved again. Then there was added 100 g microcrystalline cellulose and 15 g hydrogenated vegetable oil. The whole was mixed well and compressed into tablets, giving 10.000 tablets, each comprising 10 mg of the active ingredient.

Coating

To a solution of 10 g methyl cellulose in 75 ml of denaturated ethanol there was added a solution of 5 g of ethyl cellulose in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension and the whole was homogenated. The tablet cores were coated with the thus obtained mixture in a coating apparatus.

Example D.2: 2% Topical Cream

To a solution of 200 mg hydroxypropyl β-cyclodextrine in purified water is added 20 mg of A.I. while stirring. Hydrochloric acid is added until complete dissolution and next sodium hydroxide is added until pH 6.0. While stirring, 50 mg glycerol and 35 mg polysorbate 60 are added and the mixture is heated to 70° C. The resulting mixture is added to a mixture of 100 mg mineral oil, 20 mg stearyl alcohol, 20 mg cetyl alcohol, 20 mg glycerol monostearate and 15 mg sorbate 60 having a temperature of 70° C. while mixing slowly. After cooling down to below 25° C., the rest of the purified water q.s. ad 1 g is added and the mixture is mixed to homogenous.

What is claimed is:

1. A compound having the formula

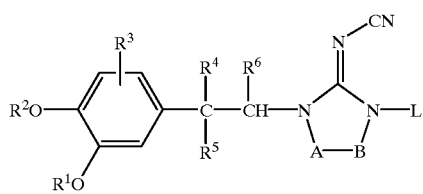

(I)

a N-oxide form, a pharmaceutically acceptable acid or base addition salt or a stereochemically isomeric form thereof, wherein:

$R^1$ and $R^2$ each independently are hydrogen; $C_{1-6}$alkyl; difluoromethyl; trifluoromethyl; $C_{3-6}$cycloalkyl; a saturated 5-, 6- or 7-membered heterocycle containing one or two heteroatoms selected from oxygen, sulfur or nitrogen; indanyl; 6,7-dihydro-5H-cyclopentapyridinyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, indanyl, 6,7-dihydro-5H-cyclopentapyridinyl, $C_{3-7}$cycloalkyl and a saturated 5-, 6- or 7-membered heterocycle containing one or two heteroatoms selected from oxygen, sulfur or nitrogen;

$R^3$ is hydrogen, halo or $C_{1-6}$alkyloxy;

$R^4$ is hydrogen; halo; $C_{1-6}$alkyl; trifluoromethyl; $C_{3-6}$cycloalkyl; carboxyl; $C_{1-4}$alkyloxycarbonyl; $C_{3-6}$cycloalkylaminocarbonyl; aryl; $Het^1$; or $C_{1-6}$alkyl substituted with cyano, amino, hydroxy, $C_{1-4}$alkylcarbonylamino, aryl or $Het^1$; or $R^4$ is a radical of formula:

wherein $R^7$ is hydrogen; $C_{1-6}$alkyl; $C_{1-6}$alkyl substituted with hydroxy, carboxyl, $C_{1-4}$alkyloxycarbonyl, amino, mono- or di($C_{1-4}$alkyl)amino, $Het^1$ or aryl;

$R^8$ is hydrogen; $C_{1-6}$alkyl; $C_{1-4}$alkylcarbonyl; $C_{1-6}$alkyl substituted with hydroxy, carboxyl, $C_{1-4}$alkyloxycarbonyl, amino, mono- or di($C_{1-4}$alkyl)amino, $Het^1$ or aryl;

$R^5$ is hydrogen, halo, hydroxy, $C_{1-6}$alkyl or $C_{1-6}$alkyloxy; or $R^4$ and $R^5$ taken together form a bivalent radical of formula:

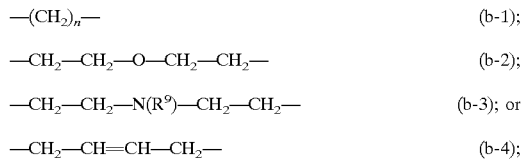

wherein n is 2, 3, 4 or 5;

$R^9$ is hydrogen, $C_{1-6}$alkyl, $C_{1-6}$alkylsulfonyl or p-toluenesulfonyl;

$R^6$ is a hydrogen or $C_{1-4}$alkyl; or $R^4$ and $R^6$ taken together may form a bivalent radical of formula —$(CH_2)_m$—;

wherein m is 1, 2, 3 or 4;

—A—B— is a bivalent radical of formula:

wherein each $R^{10}$ and $R^{11}$ independently is hydrogen or $C_{1-4}$alkyl; and L is hydrogen; $C_{1-6}$alkyl; $C_{1-6}$alkylcarbonyl; $C_{1-6}$alkyloxycarbonyl; $C_{1-6}$alkyl substituted with one or two substituents selected from the group consisting of hydroxy, $C_{1-4}$alkyloxy, $C_{1-4}$alkyloxycarbonyl, mono- and di($C_{1-4}$alkyl)amino, aryl and $Het^2$; $C_{3-6}$alkenyl; $C_{3-6}$alkenyl substituted with aryl; piperidinyl; piperidinyl substituted with $C_{1-4}$alkyl or aryl$C_{1-4}$alkyl; $C_{1-6}$alkylsulfonyl or arylsulfonyl;

aryl is phenyl or phenyl substituted with one, two or three substituents selected from halo, hydroxy, $C_{1-4}$alkyl, $C_{1-4}$alkyloxy, $C_{3-6}$cycloalkyl, trifluoromethyl, amino, nitro, carboxyl, $C_{1-4}$alkyloxycarbonyl and $C_{1-4}$alkylcarbonylamino;

$Het^1$ is pyridinyl; pyridinyl substituted with $C_{1-4}$alkyl; furanyl; furanyl substituted with $C_{1-4}$alkyl; thienyl; thienyl substituted with $C_{1-4}$alkylcarbonylamino; hydroxypyridinyl, hydroxypyridinyl substituted with $C_{1-4}$alkyl or $C_{1-4}$alkoxy-$C_{1-4}$alkyl; imidazolyl; imidazolyl substituted with $C_{1-4}$alkyl; thiazolyl; thiazolyl substituted with $C_{1-4}$alkyl; oxazolyl; oxazolyl substituted with $C_{1-4}$alkyl; isoquinolinyl; isoquinolinyl substituted with $C_{1-4}$alkyl; quinolinonyl, quinolinonyl substituted with $C_{1-4}$alkyl; morpholinyl; piperidinyl; piperidinyl substituted with $C_{1-4}$alkyl, $C_{1-4}$alkyloxycarbonyl or aryl$C_{1-4}$alkyl; piperazinyl; piperazinyl substituted with $C_{1-4}$alkyl, $C_{1-4}$alkyloxycarbonyl or aryl$C_{1-4}$alkyl; and Het$^2$ is morpholinyl; piperidinyl; piperidinyl substituted with $C_{1-4}$alkyl or aryl$C_{1-4}$alkyl; piperazinyl; piperazinyl substituted with $C_{1-4}$alkyl or aryl$C_{1-4}$alkyl; pyridinyl; pyridinyl substituted with $C_{1-4}$alkyl; furanyl; furanyl substituted with $C_{1-4}$alkyl; thienyl or thienyl substituted with $C_{1-4}$alkyl or $C_{1-4}$alkylcarbonylamino.

2. A compound according to claim 1 wherein $R^1$ and $R^2$ each independently are hydrogen; $C_{1-6}$alkyl; difluoromethyl; trifluoromethyl; $C_{3-6}$cycloalkyl; a saturated 5-, 6- or 7-membered heterocycle containing one or two heteroatoms selected from oxygen, sulfur or nitrogen; indanyl; bicyclo[2.2.1]-2-heptenyl; bicyclo[2.2.1]heptanyl; $C_{1-6}$alkylsulfonyl; arylsulfonyl; or $C_{1-10}$alkyl substituted with one or two substituents each independently selected from aryl, pyridinyl, thienyl, furanyl, $C_{3-7}$cycloalkyl and a saturated 5-, 6- or 7-membered heterocycle containing one or two heteroatoms selected from oxygen, sulfur or nitrogen.

3. A compound according to claim 1 wherein $R^1$ and $R^2$ are each independently $C_{1-6}$alkyl; $C_{3-6}$cycloalkyl; difluoromethyl; a saturated 5-, 6- or 7-membered heterocycle containing one or two heteroatoms selected from oxygen, sulfur or nitrogen; indanyl; or $C_{1-10}$alkyl substituted with aryl, indanyl, 6,7-dihydro-5H-cyclopentapyridinyl or $C_{3-6}$cycloalkyl.

4. A compound according to claim 1 wherein $R^4$ is $C_{1-6}$alkyl.

5. A compound according to claim 1 wherein $R^1$ is cyclopentyl, tetrahydrofuranyl, cyclopropylmethyl, 5-phenylpentyl, 6,7-dihydro-5H-cyclopenta[b]pyridinyl or indanyl; $R^2$ is methyl or difluoromethyl; and $R^3$, $R^5$, $R^6$, $R^{10}$, $R^{11}$ and L are hydrogen.

6. A compound according to claim 1 wherein the compound is

[1-[2-[4-(difluoromethoxy)-3-[(tetrahydro-3-furanyl)oxy]phenyl]propyl]-1,3-dihydro-2H-imidazol-2-ylidene]cyanamide; and

[1-[2-[4-(methoxy)-3-[(1,3-dihydro-2H-inden-2-yl)oxy]phenyl]propyl]-1,3-dihydro-2H-imidazol-2-ylidene]cyanamide, or a N-oxide, a stereochemically isomeric form or a pharmaceutically acceptable additon salt thereof.

7. A composition comprising a pharmaceutically acceptable carrier, and as active ingredient a therapeutically effective amount of a compound as claimed in claim 1.

8. A process of preparing a composition comprising intimately mixing a pharmaceutically acceptable carrier with a therapeutically effective amount of a compound as claimed in claim 1.

9. A method of treating a warm-blooded animal suffering from an asthmatic or atopic disease comprising administering to the warm-blooded animal a therapeutically effective amount of the compound of claim 1.

\* \* \* \* \*